United States Patent [19]

Weeks

[11] Plant 4,583

[45] Jul. 29, 1980

[54] ROSE PLANT

[76] Inventor: O. L. Weeks, 926 W. Philadelphia, Ontario, Calif. 91761

[21] Appl. No.: 22,968

[22] Filed: Mar. 22, 1979

Related U.S. Application Data

[63] Continuation of Ser. No. 848,724, Nov. 4, 1977, abandoned.

[51] Int. Cl.[3] ..... A01H 5/00

[52] U.S. Cl. ..... Plt./12

[58] Field of Search ..... Plt./12

*Primary Examiner*—Robert E. Bagwill
*Assistant Examiner*—James R. Feyrer
*Attorney, Agent, or Firm*—Frank B. Robb

[57] ABSTRACT

A hybrid tea rose plant of unusual red shade which is quite dark yet having brightness and life, reverse of petals being a yellowish cream distinguishing from other rose plants in a garden or decorative arrangement, the buds being long, tapered and formal, growing on upright, tall stems, with shiny waxy foliage.

1 Drawing Figure

This application is a continuation of application Ser. No. 848,724 filed Nov. 4, 1977, now abandoned.

DESCRIPTION OF THE INVENTION

Having carried on an extensive program of hybridization for many years in an endeavor to create new, attractive, and distinctive rose plants, the present invention relating to a new and distinct variety of hybrid tea rose plant is one of the results of this complex breeding, which has produced a very attractive rose which is identified in my records as 76-R-44 by number and "Standout" by name being the result of crossing a seed parent known as "Tiffany", U.S. Plant Pat. No. 1,304, with the pollen parent "Suspense", U.S. Plant Pat. No. 1,944, being readily distinguished from either.

My new variety, as herein described is distinguished from its parents and from all other rose varieties with which I am familiar as evidenced by the following unique combination of principal characteristics which are outstanding in said variety:

(1) The unusal red shade of the flowers, which although quite dark has brightness and life;

(2) The reverse of the petals is a yellowish cream being thereby a definite bi-color;

(3) The long, tapered, formal bud;

(4) The classic open flower when fully developed;

(5) The upright, tall, good growing plant formation; and (6) Shiny, waxy foliage.

When my new variety of rose plant is compared with the seed parent "Tiffany" it is noted that my new variety is a definite bi-color of darker yet bright inside petal having a creamy overlay on the outside, whereas "Tiffany" is more of a pink blend with whitish or slightly creamy petal base.

Further my new variety produces a much longer, tapered and more formal bud, which opens to a more classically formed flower.

My new variety is readily distinguished from the pollen parent "Suspense" since my new variety is a bi-color of darker red than the bi-color parent which is a lighter brighter red with a straw-yellow reverse petal combination.

My new variety has more formal flowers, smaller and without the ruffles of the parent, the plant of my new variety being more upright and taller with better growth habit.

Further my new variety has more shiny, waxy foliage than "Suspense".

I have effected asexual reproduction of my new variety by budding, at Chino, Calif., observed that the foregoing characteristics and distinctions come true to form and are established and transmitted through succeeding generations by such propagation.

The accompanying drawing shows typical specimens of the vegatative growth and flowers of my new variety in different stages of development, and as depicted in color as nearly true as it is reasonably possible to make the same in a color illustration of this character.

Further the following detailed description of my new variety, with color terminology in accordance with The Nickerson Color Fan, published by Munsell Color Company of Baltimore, Md., the color comparisons were made using incandescant-daylight bulb, Daylight 5,000 Degree K., and are as nearly accurate as possible to determine, general color terms of ordinary dictionary significance being used where I believe them to be appropriate:

Type: Hardy; tall; for greenhouse or outdoors; for cut flowers and garden decoration.

Class: Hybrid tea.

Breeding: Seedling.

*Seed parent.*—"Tiffany" U.S. Plant Pat. No. 1,304.

*Pollen parent.*—"Suspense" U.S. Plant Pat. No. 1,944.

Propagation: Holds its distinguishing characteristics through successive propagation by budding.

FLOWERS

Locality where grown and observed: Ontario and Chino, Calif.

Flowers borne: Singly, to 4 and 5 to a stem in irregular rounded, pyramidal, clusters; on strong medium stems.

Quantity of bloom: Abundant outdoors and in the greenhouse.

Continuity: Intermittent to continuous.

Fragrance: Slight.

Bud:

*Peduncle.*—Medium length; heavy caliper; erect; entirely rough; few to numerous red prickles. Color — medium yellowish green.

*Before calyx breaks.*—Size — medium to small. Form — short to medium length; oval; without a conspicuous neck; with foliaceous appendages on the surface of the bud; with slender cut foliaceous parts extending beyond the tip of the bud equal to ½ to ¾ or more of its length. Color — yellowish green with greenish bronze tips.

*As calyx breaks.*—Color — yellowish green with veins of bronze extending its full length.

*As petals first open.*—Size — medium to large. Form — long and ovoid. Opening — opens up well.

Bloom:

*Size (when fully open).*—Medium, from 3 inches to 4½ inches.

*Petalage.*—Very double; from 45 to 50 petals arranged regularly.

*Form.*—Very high centered; at first; becoming open to cupped and high centered; petals being at first tightly rolled upward; becoming later at maturity tightly cupped, rolled outward.

Petals:

*Texture.*—Moderately thick; leathery; with inside velvety.

*Appearance.*—Inside velvety; outside satiny.

*Shape.*—Outside — orbicular; slightly scalloped with 1 to 2 notches. Intermediate — orbicular; slightly scalloped with 1 to 2 notches. Inside — orbicular; slightly scalloped with 1 to 2 notches.

This description of a newly opened flower was made from a rose grown outdoors at Ontario, Calif.:

*Color.*—Outer petal — outside surface — lower segment brilliant greenish yellow 7.5Y9/8. Petal moderate yellowish pink 10R8/6 but lighter with minute veins of strong purplish pink 7.5RP7/10 but lighter. Inside surface — bottom segment a brilliant yellow 5Y9/9 but darker. Petal between strong red 5R4/12 and strong purplish red 7.5RP5/12 but lighter. Intermediate petal — outside surface — bottom segment is near brilliant yellow green 2.5GY9/8. Petal moderate pink 5R8/6 but lighter with minute veins of strong purplish pink 7.5RP7/10 but lighter. Inside surface — lower segment near brilliant yellow 2.5Y9/9. Petal is a blend of strong red 5R4/12 and strong purplish red 7.5RP5/12. Inner petal — outside surface — lower segment near bright yellow green 2.5 GY9/8. Petal a blending of moderate orange yellow 7.5YR8/8 but lighter and a strong red 2.5R5/12 but lighter and a strong red 5R4/12. Inside surface—lower segment near vivid greenish yellow 7.5Y6/12 but lighter. Petal strong red 5R4/12 but darker blended with a strong purplish red 10RP4/12 but lighter.

The following description was made from a rose that was opened for three days outdoors at Ontario, Calif.:

*Color.*—Outer petal — outside surface — lower segment near brilliant greenish yellow 7.5Y8/9 but darker. Inside surface — lower segment near vivid greenish yellow 7.5Y8/12. Petal strong red 5R4/12 blended with moderate purplish red 5RP5/10 but lighter. Inner petal — outside surface — lower segment near brilliant greenish yellow 7.5Y9/8 but darker. Petal moderate yellowish pink 10R8/6 but lighter with minute veins of strong purplish pink 7.5RP7/10 but lighter. Inside surface — bottom segment is near brilliant greenish yellow 7.5Y9/8 but darker. Petal a blend of strong red 5R4/12 but lighter and moderate purplish red 5RP5/10 but lighter with margin of strong purplish pink 5RP7/9 but lighter. General color effect — newly opened flower — deep purplish pink combined with a strong red noting a yellowish cream reverse petal coloration. Three days open — through a range of deep purplish pink to a strong red but lighter. Ridges show as strong purplish pink.

*Behavior.*—Drop off cleanly.

*Flower longevity.*—On bush in garden — 3 to 5 days in October. Cut roses grown outdoors kept at living room temperatures 3 to 5 days in October.

REPRODUCTIVE ORGANS

Stamens: Very few; arranged irregularly about pistils; mixed with petaloids; tucked in calyx.

Filaments: Medium to long; most with anthers.

*Color.*—Yellow.

Anthers: Medium size; all open at various times.

*Color.*—Yellow.

Pollen: Moderate.

*Color.*—Lemon yellow.

Pistils: Many.

Styles: Short to medium length; medium caliper; very bunched.

Stigma:

*Color.*—White.

Ovaries: All enclosed in calyx.

Hips: None observed.

Sepals: Permanent; very curled.

*Color.*—Yellowish green with light bronze strip in center.

Seeds: None observed.

PLANT

Foliage:

*Leaves.*—Compound of 5 to 7 leaflets; moderately abundant; medium size to large; moderately heavy; leathery; glossy.

*Leaflets.— Shape —obtuse apex; margin irregularly serrate.*

*Color.*—Mature — upper surface — between dark yellowish green 10GY4/5 and dark grayish green 10GY3/2. Under surface — between strong yellow green 7.5GY7/9 and 7.5GY6/8. Young — upper surface — between dark yellowish green 10GY4/5 and dark grayish green 10GY3/2 with veins and edges dark red 5R3/7. Under surface — between dark greenish yellow 10Y6/7 and light olive 10Y5/5 with dark red 5R3/7 more predominant.

*Rachis.*—(The supporting stem of the compound leaf) — light to medium weight. Upper side — smooth; grooved. Under side — somewhat thorny.

*Stipules.*—Long; narrow; short to medium points; turning out at an angle of more than 45 degrees.

*Disease and insect resistance.*—Average resistance to powdery mildew.

Growth:

*Habit.*—Upright; much branched.

*Growth.*—Moderately to vigorous.

*Canes.*—Medium caliper.

*Main stems.*—Color — dull grey green. Large prickles — several; short to medium length; slightly hooked downward with long narrow base. Color — brown. Small prickles — few. Color — brown. Hairs — none.

*Branches.*—Color — Dull grey green. Large prickles — few; medium; hooked downward with long narrow base. Color — brown. Small prickles — none. Hairs — none.

*New shoots.*—Color — bright yellowish green with some bronze. Large prickles — short to medium length; hooked downward with long narrow base. Color — reddish with light yellow tips.

Small prickles — many. Color — reddish. Hairs — reddish.

I claim:

1. A new and distinct variety of rose plant of the hybrid tea class, substantially as herein shown and described, characterized particularly as to novelty by the unique combination of inside petals of a dark red shade of peculiar brightness and life, with reverse of the petals yellowish cream producing a bicolor effect, with long, tapered formal buds, upright, tall plant habit, and waxy shiny foliage with generally better growth than the parents.

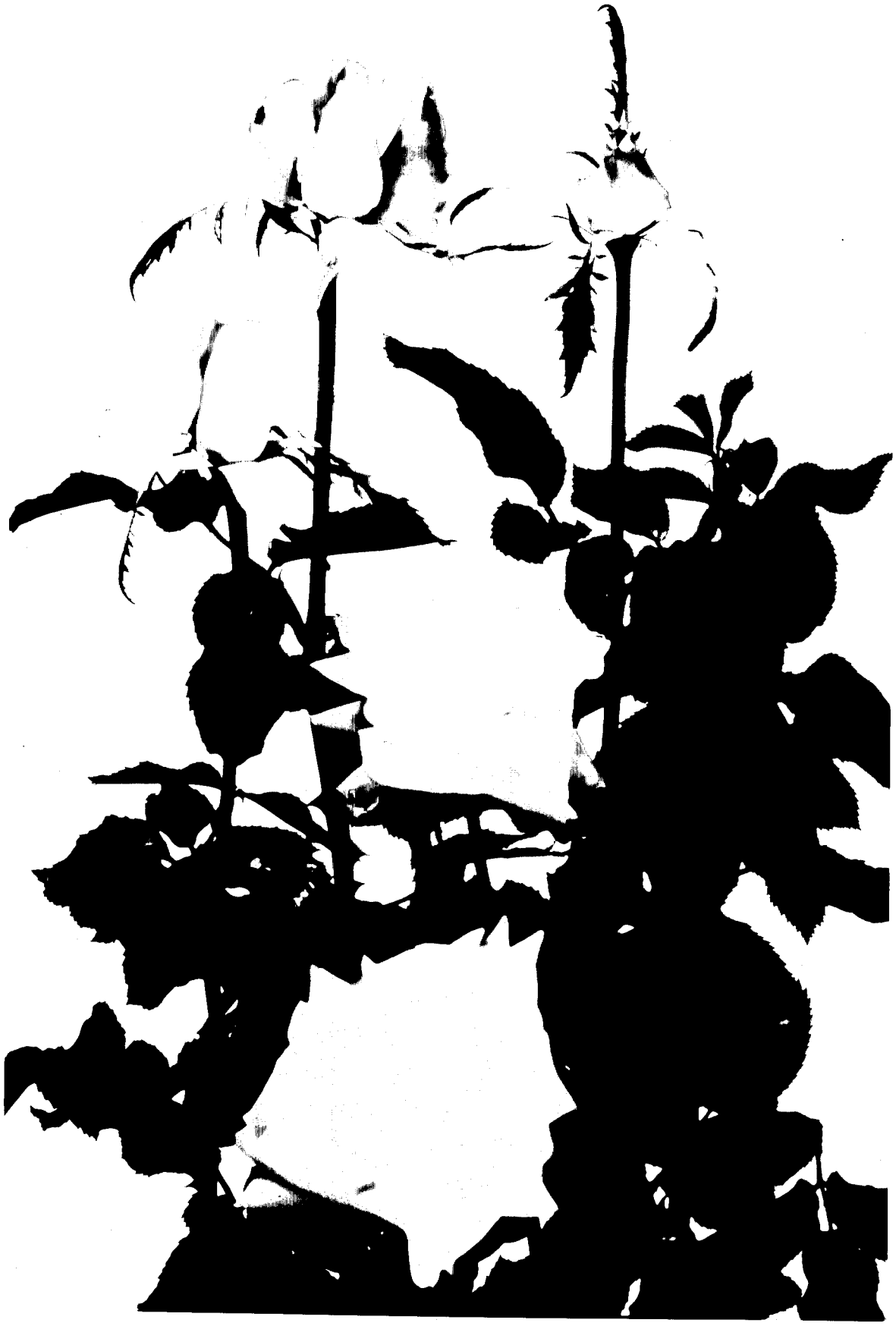

* * * * *